(12) United States Patent
Byun et al.

(10) Patent No.: US 10,207,986 B2
(45) Date of Patent: Feb. 19, 2019

(54) METHOD FOR PREPARING D-ARGININE

(71) Applicant: Aminologics Co., Ltd., Seoul (KR)

(72) Inventors: Il-Suk Byun, Seongnam (KR); Won-Sup Kim, Seongnam (KR); Hye-Lim Ga, Seoul (KR); Jung-Ho Lee, Incheon (KR)

(73) Assignee: Aminiologics Co., Ltd., Seoul (KR)

( * ) Notice: Subject to any disclaimer, the term of this patent is extended or adjusted under 35 U.S.C. 154(b) by 0 days.

(21) Appl. No.: 15/504,602

(22) PCT Filed: Aug. 5, 2015

(86) PCT No.: PCT/KR2015/008211
§ 371 (c)(1),
(2) Date: Feb. 16, 2017

(87) PCT Pub. No.: WO2016/028016
PCT Pub. Date: Feb. 25, 2016

(65) Prior Publication Data
US 2017/0233334 A1    Aug. 17, 2017

(30) Foreign Application Priority Data
Aug. 20, 2014 (KR) .................. 10-2014-0108401

(51) Int. Cl.
*C07C 277/08* (2006.01)

(52) U.S. Cl.
CPC .................. *C07C 277/08* (2013.01)

(58) Field of Classification Search
None
See application file for complete search history.

(56) References Cited

U.S. PATENT DOCUMENTS

| | | | |
|---|---|---|---|
| 4,016,205 A * | 4/1977 | Kariyone | C07B 57/00 562/100 |
| 4,215,223 A | 7/1980 | Kessels | |
| 4,434,107 A * | 2/1984 | Chibata | C07C 227/34 562/401 |
| 5,496,955 A | 3/1996 | Becker et al. | |
| 5,591,613 A | 1/1997 | Makryaleas et al. | |
| 6,310,242 B1 | 10/2001 | Noda et al. | |
| 8,835,676 B2 | 9/2014 | Divi et al. | |

FOREIGN PATENT DOCUMENTS

| | | |
|---|---|---|
| EP | 0119804 A1 | 9/1984 |
| GB | 842839 A | 7/1960 |

(Continued)

OTHER PUBLICATIONS

International Search Report in PCT International Application No. PCT/KR2015/008211, dated Aug. 5, 2015.

(Continued)

*Primary Examiner* — Clinton A Brooks
*Assistant Examiner* — Jennifer C Sawyer
(74) *Attorney, Agent, or Firm* — Venable LLP; Henry J. Daley; Miguel A. Lopez

(57) ABSTRACT

Disclosed is a method of preparing D-arginine, wherein D-arginine is obtained by the optical resolution of DL-arginine using D-3-bromocamphor-10-sulfonic acid as an optical resolving agent.

3 Claims, 1 Drawing Sheet

(56) References Cited

FOREIGN PATENT DOCUMENTS

JP          10-80297 A       3/1998
JP       2011-167107 A       9/2011

OTHER PUBLICATIONS

Levintow et al., "Preparation of D-ornithine, D-citrulline, and D-arginine," J. Biol. Chem., 1951.
Birnbaum et al., "Preparation of the Optical Isomers of Arginine, Histidine and S-Benzylcysteine by Asymmetric Enzymatic Hydrolysis of their Acetyl Derivatives," Archives of Biochemistry and Biophysics, 1952.
Birnbaum et al., "A Simplified Preparation of D-arginine," Archives of Biochemistry and Biophysics, 1956.
Nadai, "Studies on Arginase: I. Enzymatic Resoluation of dl-Arginine into its Optical Antipodes," The Journal of Biochemistry, 1958.
Berg et al., "A simple method of preparing d-(−)-Arginine monohydrochloride from dl-Arginine," Analytical Biochecmistry, 1975.

* cited by examiner

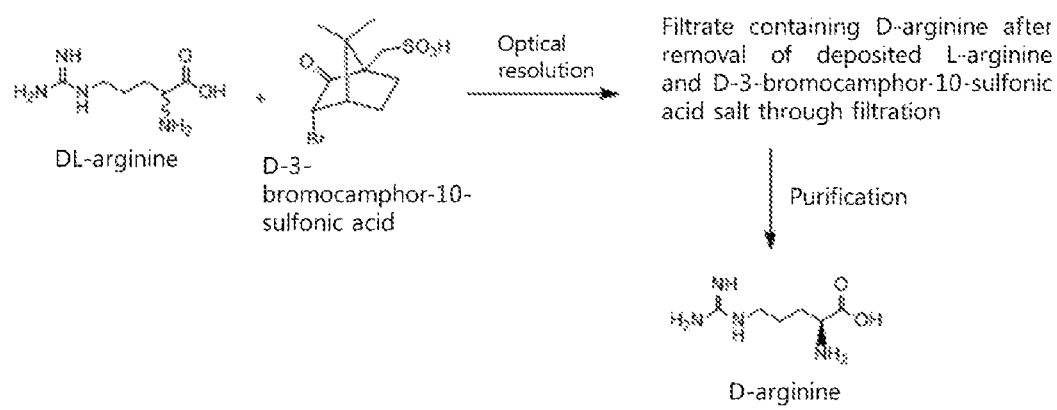

METHOD FOR PREPARING D-ARGININE

TECHNICAL FIELD

The present invention relates to a method of preparing D-arginine, and more particularly to a method of preparing D-arginine by the optical resolution of DL-arginine using D-3-bromocamphor-10-sulfonic acid as an optical resolving agent.

BACKGROUND ART

D-arginine is an essential ingredient used for producing medicaments such as an enuresis therapeutic agent Desmopressin, a hereditary angioedema therapeutic agent Icatibant, and a hyperparathyroidism therapeutic agent Velcalcetide.

Conventional techniques for preparing D-arginine are largely classified into two types, one of which is a biological optical resolution process using an enzyme, and the other of which is a chemical optical resolution process using a chiral organic acid.

A method of preparing D-arginine through a biological optical resolution, including selectively obtaining D-acetyl-arginine from DL-acetyl-arginine through a optical resolution using an enzyme and then hydrolyzing the D-acetyl-arginine, is known in [Archives of Biochemistry Biophysics, 39, 108(1952); Archives of Biochemistry Biophysics, 60, 496(1956); The Journal of Biochemistry, 45(9), 687 (1958)], but is problematic because many process steps are performed and the hydrolysis of D-acetyl-arginine, obtained through optical resolution, corresponding to a key step, in a hydrochloric acid aqueous solution is required.

As an additional enzyme-assisted technique, U.S. Pat. No. 5,591,613 discloses a method of preparing D-arginine by selectively decomposing L-arginine of DL-arginine into L-ornithine using an enzyme. However, this method is disadvantageous in that L-arginine contained in DL-arginine is not recovered but is decomposed.

On the other hand, a chemical optical resolution using a chiral organic acid is advantageous in that chemical processing is performed using a simple apparatus and is easy, compared to biological processing, and is thus suitable for mass production. Here, appropriately selecting the chiral organic acid that serves as the optical resolving agent is very important but is difficult.

Analytical Biochemistry, 63, 68(1975) has reported that, in order to prepare D-arginine from DL-arginine, optical resolving agents such as tartaric acid, camphoric acid and glutamic acid have been employed but have failed to obtain desired results, and also that D-arginine may be separated and obtained using L-malic acid. However, complicated processing, including crystallizing an aqueous solution of DL-arginine and L-malic acid for one day in a refrigerator to thus afford a primary crystal, which is then concentrated to give a secondary crystal, has to be carried out. In particular, only the specific optical rotation ($[\alpha]_D$) of the obtained D-arginine is mentioned, and instrumental analysis by chiral chromatography is not provided, making it difficult to accurately confirm the optical purity of the obtained D-arginine, which is undesirable.

DISCLOSURE

Technical Problem

Accordingly, the present invention has been made keeping in mind the problems encountered in the related art, and the present invention is intended to provide a method of preparing D-arginine by the optical resolution of DL-arginine using, as an optical resolving agent, D-3-bromocamphor-10-sulfonic acid, having an excellent optical resolving effect among chiral organic acids.

Technical Solution

The present invention provides a method of preparing D-arginine, comprising:
(1) removing L-arginine and a D-3-bromocamphor-10-sulfonic acid salt, deposited by the optical resolution of DL-arginine using D-3-bromocamphor-10-sulfonic acid; and
(2) purifying D-arginine that is left behind in a filtrate from which deposits are removed.

Advantageous Effects

According to the present invention, a method of preparing D-arginine is capable of obtaining D-arginine by the optical resolution of DL-arginine using D-3-bromocamphor-10-sulfonic acid, which has an excellent optical resolving effect, as an optical resolving agent, thus increasing the optical purity of D-arginine, simplifying the preparation process to thus generate economic benefits, and enabling the mass production of D-arginine.

BRIEF DESCRIPTION OF DRAWING

FIG. 1 schematically shows a process of preparing D-arginine according to the present invention.

BEST MODE

Hereinafter, a detailed description will be given of the present invention.

Typically, in order to prepare D-arginine through chemical optical resolution of DL-arginine, a chiral organic acid is used as an optical resolving agent. Here, selecting a chiral organic acid suitable therefor is regarded as very difficult. A conventionally used chiral organic acid is problematic because the process steps for preparing D-arginine are complicated and the optical purity thereof cannot be confirmed.

Accordingly, the present inventors have studied the optical resolving effects of DL-arginine using various kinds of chiral organic acid as the optical resolving agent, resulting in the finding that D-3-bromocamphor-10-sulfonic acid is able to exhibit an excellent optical resolving effect, and thus DL-arginine is optically resolved by using D-3-bromocamphor-10-sulfonic acid, thereby obtained D-arginine.

Specifically, the present invention addresses a method of preparing D-arginine by the optical resolution of DL-arginine using D-3-bromocamphor-10-sulfonic acid as an optical resolving agent, and D-arginine may be prepared through the following steps of (1) removing L-arginine and a D-3-bromocamphor-10-sulfonic acid salt, deposited by the optical resolution of DL-arginine using D-3-bromocamphor-10-sulfonic acid, and (2) purifying D-arginine left behind in a filtrate from which deposits are removed.

In step (1), D-3-bromocamphor-10-sulfonic acid is used in an amount of 0.1 to 1.5 equivalents, and preferably 0.6 to 1.1 equivalents, based on the amount of DL-arginine. If the amount of D-3-bromocamphor-10-sulfonic acid is less than 0.1 equivalents, optical resolving efficiency may decrease.

On the other hand, if the amount thereof exceeds 1.5 equivalents, the yield of D-arginine may decrease.

Also, D-3-bromocamphor-10-sulfonic acid may be used in various forms, and the form thereof is not particularly limited, but preferably useful is at least one selected from the group consisting of a D-3-bromocamphor-10-sulfonic acid hydrate and a D-3-bromocamphor-10-sulfonic acid ammonium salt.

DL-arginine is optically resolved into D-arginine and L-arginine by means of the optical resolving agent, namely D-3-bromocamphor-10-sulfonic acid, and D-3-bromocamphor-10-sulfonic acid is converted into a D-3-bromocamphor-10-sulfonic acid salt. More particularly, L-arginine and the D-3-bromocamphor-10-sulfonic acid salt are deposited in a solid phase, and D-arginine is left behind in a state of being dissolved in a reaction solution.

In order to obtain only D-arginine, in step (1), L-arginine and the D-3-bromocamphor-10-sulfonic acid salt, which are deposits, are removed through filtration, and only D-arginine is left behind in the filtrate.

In step (2), D-arginine left behind in the filtrate is purified, finally yielding D-arginine. Here, the purification process may be carried out through various known typical processes, and preferably using an ion exchange resin.

Specifically, D-arginine may be purified through typical ion exchange resin processing in a manner in which the filtrate containing D-arginine left behind therein is concentrated, dissolved in water, adsorbed into an ion exchange resin, desorbed using an ammonia aqueous solution, and then concentrated.

In addition to the ion exchange resin, an isoelectric point process may be performed, and more specifically, D-arginine may be purified in a manner such that D-arginine is basified to pH 10.8, corresponding to the isoelectric point of D-arginine, and then added with an organic solvent such as alcohol.

D-arginine thus prepared may be analyzed in its optical purity using a chiral column.

A better understanding of the present invention may be obtained via the following examples, which are set forth to illustrate, but are not to be construed as limiting the scope of the present invention.

MODE FOR INVENTION

<Preparation of D-Arginine>

EXAMPLE 1

DL-arginine (42.5 g, 244 mmol) and D-3-bromocamphor-10-sulfonic acid monohydrate (60.3 g, 183 mmol, 0.75 equivalents (eq.)) were added to 1300 mL of methanol, heated to 60° C. so as to be dissolved, and then slowly cooled.

The resulting solution was stirred at room temperature for 2 hr, and the deposited L-arginine and D-3-bromocamphor-10-sulfonic acid salt were filtered off.

Thereafter, the remaining filtrate was concentrated, dissolved in 500 mL of distilled water, passed through a column filled with an ion exchange resin (IRC-86, NH4 type) to adsorb D-arginine, and washed with distilled water. The adsorbed D-arginine was desorbed using 5% ammonia water, and the desorbed aqueous solution was concentrated again, thereby obtaining D-arginine.

The optical purity of D-arginine thus obtained was analyzed using a chiral column (Sumichiral OA-5000 column), and the analysis conditions were as follows.

Column: Sumichiral OA-5000 (5 μm, 4.6±250 mm)
Mobile phase: Solution of 2% acetonitrile dissolved in 2 mM $CuSO_4$ solution
Detector: UV (254 nm)

Based on the results of analysis of the optical purity of D-arginine under the above analysis conditions, D-arginine obtained in an amount of 15.5 g was configured such that D-arginine and L-arginine were present at a ratio of 95:5.

Also, the results of $^1$H-NMR of the obtained D-arginine were as follows.

$^1$H-NMR ($D_2O$, 400 MHz): δ 1.43 (m, 4H), 3.02 (m, 2H), 3.09 (m, 1H)

EXAMPLES 2 TO 4

D-arginine was prepared in the same manner as in Example 1, with the exception that the D-3-bromocamphor-10-sulfonic acid monohydrate was used in amounts of 0.6, 0.7 and 1 equivalents (eq.) in Examples 2, 3 and 4, respectively, and the optical purity of the prepared D-arginine was analyzed using a chiral column, as in Example 1.

The results of the optical purity of D-arginine prepared in Examples 1 to 4 are shown in Table 1 below.

TABLE 1

| | Amount (eq.) of D-3-bromocamphor-10-sulfonic acid monohydrate | D-arginine-to-L-arginine ratio in filtrate |
| --- | --- | --- |
| Ex. 1 | 0.75 eq. | 95:5 |
| Ex. 2 | 0.6 eq. | 85:15 |
| Ex. 3 | 0.7 eq. | 92:8 |
| Ex. 4 | 1.0 eq. | 97:3 |

As is apparent from the results of Table 1, when the amount (eq.) of the D-3-bromocamphor-10-sulfonic acid monohydrate used as the optical resolving agent in the present invention was increased, the optical resolving effect of DL-arginine was raised, thus increasing the optical purity of D-arginine.

Also, when D-arginine obtained in Example 1 was additionally recrystallized using a mixed solution of 16 mL of water and 140 mL of methanol, D-arginine (12.4 g, D-arginine/L-arginine=99.3/0.7) having further improved optical purity could be obtained.

EXAMPLES 5 TO 7

D-arginine was prepared in the same manner as in Example 1, with the exception that a D-3-bromocamphor-10-sulfonic acid ammonium salt was used as the optical resolving agent, in lieu of the D-3-bromocamphor-10-sulfonic acid monohydrate, and was used in amounts of 0.9, 1 and 1.1 equivalents (eq.) in Examples 5, 6 and 7, respectively, and the optical purity of the prepared D-arginine was analyzed using a chiral column, as in Example 1. The results are shown in Table 2 below.

TABLE 2

| | Amount (eq.) of D-3-bromocamphor-10-sulfonic acid ammonium salt | D-arginine-to-L-arginine ratio in filtrate |
| --- | --- | --- |
| Ex. 5 | 0.9 eq. | 95:5 |
| Ex. 6 | 1.0 eq. | 96:4 |
| Ex. 7 | 1.1 eq. | 97:3 |

Similar to the results of Examples 1 to 4, when the amount (eq.) of the D-3-bromocamphor-10-sulfonic acid ammonium salt used as the optical resolving agent was increased, the light-splitting effect of DL-arginine was raised, thus increasing the optical purity of D-arginine.

Consequently, the present invention, which pertains to the preparation of D-arginine by light-splitting DL-arginine using D-3-bromocamphor-10-sulfonic acid as the optical resolving agent, is advantageous in that it is characterized by a high D-arginine yield and a simple preparation process, thus enabling the mass production of D-arginine.

The invention claimed is:

1. A method of preparing D-arginine, comprising steps of:
   (1) removing L-arginine and a D-3-bromocamphor-10-sulfonic acid salt, deposited by the optical resolution of DL-arginine using D-3-bromocamphor-10-sulfonic acid; and
   (2) purifying D-arginine left behind in a filtrate from which deposits are removed,
   wherein the D-3-bromocamphor-10-sulfonic acid is at least one selected from the group consisting of a D-3-bromocamphor-10-sulfonic acid hydrate and a D-3-bromocamphor-10-sulfonic acid ammonium salt,
   wherein the removing L-arginine and a D-3-bromocamphor-10-sulfonic acid salt further comprises adding the DL-arginine and the D-3-bromocamphor-10-sulfonic acid to a solvent comprising methanol, and
   wherein the solvent does not comprise isobutyl alcohol, chloroform, or toluene.

2. The method of claim 1, wherein the D-3-bromocamphor-10-sulfonic acid is used in an amount of 0.1 to 1.5 equivalents based on an amount of DL-arginine.

3. The method of claim 1, wherein the purifying the D-arginine in the step (2) is performed using an ion exchange resin.

\* \* \* \* \*